United States Patent [19]

Lewis

[11] 4,051,167
[45] Sept. 27, 1977

[54] ALPHA HALO SUBSTITUTED PEROXYESTERS AND THEIR USE AS POLYMERIZATION INITIATORS

[75] Inventor: Roger N. Lewis, Martinez, Calif.

[73] Assignee: Argus Chemical Corporation, Brooklyn, N.Y.

[21] Appl. No.: 642,432

[22] Filed: Dec. 19, 1975

Related U.S. Application Data

[63] Continuation-in-part of Ser. No. 532,966, Dec. 16, 1974, abandoned.

[51] Int. Cl.$^2$ .................... C07C 179/18; C08L 67/06
[52] U.S. Cl. .................... 260/453 RZ; 526/213; 526/227; 260/861
[58] Field of Search .................... 260/453 RZ

[56] References Cited

U.S. PATENT DOCUMENTS

| | | | |
|---|---|---|---|
| 3,082,236 | 3/1963 | Mageli | 260/453 RZ |
| 3,264,274 | 8/1966 | Leveskis | 260/453 RZ |
| 3,446,831 | 5/1969 | Mageli | 260/453 RZ |
| 3,451,989 | 6/1969 | Rekers et al. | 260/453 RZ |
| 3,542,856 | 11/1970 | Mageli et al. | 260/453 RZ |
| 3,624,123 | 11/1971 | Lewis et al. | 260/453 RZ |

FOREIGN PATENT DOCUMENTS

| | | | |
|---|---|---|---|
| 534,709 | 12/1956 | Canada | 260/453 R |

OTHER PUBLICATIONS

Fossey et al., "Thermal Decomposition of Peroidset," (1971) C. A. 75 No. 109663t(1971).

*Primary Examiner*—Lewis Gotts
*Assistant Examiner*—Robert C. Whittenbaugh
*Attorney, Agent, or Firm*—Townsend and Townsend

[57] ABSTRACT

Aliphatic peroxyester polymerization initiators whose thermal stability is controlled by a bromine or chlorine substituent on the carbon atom in the alpha position relative to the carbonyl group in the acid moity of the perester. The initiators show increased efficiency for the polymerization of methyl methacrylate, styrene, ethylene, and in curing unsaturated polyester resins. Typical is 1,1,3,3-tetramethyl butyl peroxy 2-chlorolaurate.

16 Claims, No Drawings

ALPHA HALO SUBSTITUTED PEROXYESTERS AND THEIR USE AS POLYMERIZATION INITIATORS

This is a continuation-in-part application of Ser. No. 532,966 filed Dec. 16, 1974, now abandoned.

This invention relates to organic peroxide polymerization initiators having a chlorine or bromine substituent on the carbon atom in the alpha position relative to the carbonyl group in the acid moity of the perester and their use as polymerization initiators for methyl methacrylate, styrene, ethylene, and ethylenically unsaturated polyester resins.

In accordance with the present invention, there is provided an organic peroxide of the formula:

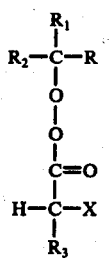

wherein each of $R_1$ and $R_2$ are alkyl of up to about 7 carbon atoms, X is selected from bromine and chlorine, $R_3$ is alkyl of up to about 18 carbon atoms provided that $R_3$ is not methyl when R is alkyl, and R is selected from alkyl of up to about 7 carbon atoms and

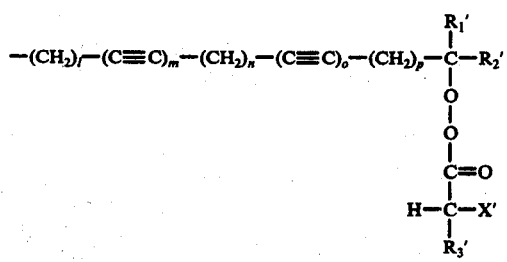

in which $l$, $m$, $n$, $o$, and $p$ are integers from 0–5 provided the sum of $l$, $m$, $n$, $o$, and $p$ is at least 1, and $R_1'$, $R_2'$ and $R_3'$ are each the same as $R_1$, $R_2$ and $R_3$, respectively.

Commonly, $R_3$ will be an alkyl group of from two to about 10 carbon atoms and may be branched or straight chain but is preferably straight chain. Where R is an alkyl group, the present peroxyesters are monoperesters. Such compounds usually will have lower alkyl groups for R, $R_1$ and $R_2$ forming, for example, a tertiary butyl group. However, higher alkyl groups are contemplated which may be straight or branched chain. For example, a preferred group formed from R, $R_1$ and $R_2$, together with the tertiary carbon atom to which they are bonded is the 1,1,3,3-tetramethyl butyl group. With this latter preferred structure, $R_3$ may be selected from methyl as well as the above described structures.

The alternative group of molecules is obtained where R is not an alkyl group but is selected to form a diperester molecule. Common diperester molecules of this invention are obtained where R has the structure

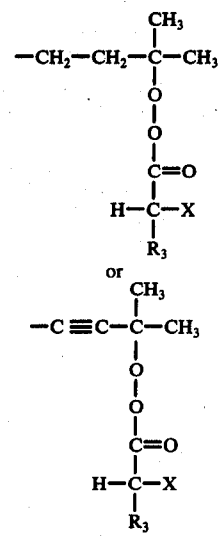

and X and $R_3$ have the above definitions.

In general, the organic monoperoxyesters and the diperoxyesters of this invention are similar to and are formed by reactions heretofore used in preparing these two types of peresters. Thus, U.S. Pat. No. 3,264,274 discloses saturated diperesters, U.S. Pat. No. 3,444,230 discloses acetylenically unsaturated diperesters, and U.S. Pat. No. 3,624,123 discloses diperesters, as well as monoperesters, analogous to the peroxides of this invention. Canadian Pat. No. 534,709 suggests the possible structure of a homologous peroxyester but its properties are not suggested and the increased efficiencies of the present molecules are not obtained therefrom. The present peroxides otherwise generally differ from said prior art peresters in that either a chlorine or bromine atom is substituted on the carbon atom positioned alpha relative to the carbonyl group of the acid forming the perester. Thus, the present peresters may be obtained by reactants and methods generally described in said U.S. patents provided that the acid halide reactant used in forming the peroxyester contains a chlorine or bromine substituent on the alpha carbon atom of the acid halide reactant.

The present peresters are especially useful for initiating the polymerization of ethylenically unsaturated monomers. Preferably, the present organic peroxides are used for the polymerization of styrene monomer, acrylate monomer, ethylene monomers, and polyester resins which can be crosslinked through ethylenic unsaturation contained therein. The process is generally similar to those of the prior art except for the use of the novel peroxyesters of this invention.

It is well known that thermal stability of a peroxide such as a peroxyester is important in the suitability of its choice as a polymerization initiator. Monomers differ in their properties and requirements for obtaining an optimum polymerization product. Among other factors the rate of polymerization may greatly influence the properties of the end polymer product. As a result, the art has continued to search for techniques for controlling the thermal stability of peroxides such as peroxyesters so as to create the ability to control polymerization rate.

It is well accepted that an index of the thermal stability of a peroxyester is its half life—the time required for half of the peroxyester to decompose. Half life may be determined at a particular temperature or at the temperature at which the peroxyester is maintained in order to achieve a half life of a particular length of time. As will be seen hereinafter, the properties of the present peresters are described in terms of the temperature at which they must be maintained to provide a ten-hour half life.

U.S. Pat. Nos. 3,542,856 and 3,770,770 describe a group of peroxyesters whose thermal stability has been controlled through substituents thereon. These prior art patents indicate the desirability of such control in terms of achieving desired polymerization rates. According to these patents, prior available peroxyesters were of limited utility in the polymerization of ethylenic monomers because of the temperature at which the polymerizations had to be carried out and the adverse effect on the properties of the polymers produced. These patents provide one solution to the problem by including certain substituents on the peroxyesters in the beta position relative to the carbonyl group. It appears from these patents that the patentees were unsuccessful in any attempts to control the thermal stability of peroxyesters with substituents on the alpha carbon atom. Contrary to such prior art teachings, the present invention provides thermally stable peroxyesters in which the alpha carbon atom has a chlorine or bromine substituent. As will be seen in the data presented below, the chlorine and bromine substituents in the alpha position are unique as compared with, for example, alkyl substituents in the alpha position. Alpha alkyl substituents provide substantially less stable peroxyesters than the present halo substituted molecules.

The present peroxyesters of which most have a ten-hour half life in the 70°-80° C range fill a relative void in the available peroxyesters. For example, tertiary butyl peroxy isobutyrate is a commercially available peroxyester whose thermal stability is similar to the present compounds. However, it is being phased out in industry due to odor problems, its hazardous nature which requires dilution in a solvent, its higher volatility and requirement of refrigerated storage. The present materials are considered as a replacement for this peroxyester.

A series of peroxyesters illustrative of this invention has been synthesized by utilizing procedures which generally follow that of the prior art for making peroxyesters. Of course, in the present case the acid halide reactant has the crucial alpha halo substituent. The following procedure for t-butyl peroxy 2-chloro laurate is typical for the synthesis of the compositions of this invention. As will be understood the other compounds are formed by selecting appropriate reactants and quantities:

EXAMPLE I

TYPICAL EXPERIMENTAL PROCEDURE: t-BUTYL PEROXY 2-CHLORO LAURATE

To a stirred mixture of 9.88 g (0.10 mole) of 91.18% t-butyl hydroperoxide (TBHP) and 40 ml petroleum ether, 11.87 g (0.15 mole) of pyridine was added slowly in 2 minutes at 7-10° C. Then 25.33 g (0.10 mole) of 93+% 2-chloro-lauroyl chloride was added dropwise to the vigorously stirred reaction mixture in 10.5 minutes at 10°-25° C. The reaction mixture was held between 22°-25° C for 29.5 minutes. At this point, the reaction mixture was filtered to remove the precipitated pyridinium hydrochloride, and the organic filtrate was transferred to a separatory funnel. Additional petroleum ether was used to wash the filter cake and rinse the Buchner filter flask and was added to the separatory funnel. The product layer was washed by shaking once with a mixture of 50 ml of cold water and 10 ml of saturated NaCl solution and once with a mixture of 50 ml of cold water and 20 ml of saturated NaCl solution. A partial emulsion formed with each wash. Then the product layer was filtered twice through a cake of anhydrous MgSO$_4$ to remove all the water and concentrated under vacuum using a 20° C water bath. IR and TLC analyses of isolated product indicated no residual hydroperoxide. Product A.O. analysis: Theory, 5.21; Found, 4.86, 4.85, 93.84% pure; 82.7% yield.

Utilizing the procedure of EXAMPLE I, the following compounds have been prepared:

Table 1

| Perester | Results of the Synthesis of Various 2-Chloroalkyl Peresters | | | | | |
|---|---|---|---|---|---|---|
| | M.W. | TAO | % Purity | % Yield | Refractive Index at 24° C | Sp. Gr. at 25.5° C |
| t-Butyl Peroxy 2-Chlorobutyrate | 194.65 | 8.22 | 99.70 | 77.7 | 1.4354 | 1.028 |
| t-Butyl Peroxy 2-Chlorooctanoate | 250.76 | 6.38 | 88.81 | 86.3 | 1.4469 | 0.975 |
| t-Butyl Peroxy 2-Chlorolaurate | 306.90 | 5.21 | 93.84 | 82.7 | 1.4501 | 0.957 |
| 1,1,3,3-Tetramethyl Butyl Peroxy 2-Chlorolaurate | 363.00 | 4.41 | 92.43 | 91.2 | 1.4533 | 0.922 |
| 2,5-Dimethyl-2,5-Di(2-Chlorolauroyl Peroxy) Hexane | 611.78 | 5.23 | 95.33 | 84.9 | Unk[1] | Unk[1] |
| 2,5-dimethyl-2,5-di(2-chlorobutyryl peroxy) hexyne-3 | 383.25 | 8.34 | 91.34 | 88.7 | 1.4692[2] | 1.093[3] |
| t-butyl peroxy 2-bromolaurate | 332.87 | 4.81 | 82.62 | 74.7 | —[4] | —[4] |

[1]Solidified at 0 to +3° C in refrigerator and remained a slush at room temperature.
[2]at 26° C
[3]at 27.5° C
[4]Not determined because of lower purity.

The properties of these compositions relative to stability have been tested with the results shown in Table 2 below:

Table 2

Physical Stablity Tests on Various 2-Chloroalkyl Peresters

| Perester | % Purity | Rapid Heat Test[1] | Burning Rate Test[2] | Shock Sensitivity[3] |
|---|---|---|---|---|
| t-Butyl Peroxy 2-Chlorobutyrate | 99.70 | Very vigorous decomposition between 107-½-115° C., with initial decomposition at 99.5° C. | 24 sec. with mild sooty flame to 1-½ft., 1 sec. to ignition. | Not sensitive |
| t-Butyl Peroxy 2-Chlorooctanoate | 88.81 | Very vigorous decomposition between 112-115° C., with initial decomposition at 107° C. | About 78 sec. with mild sooty flame to 1 ft. Match served as a wick in final portion of burning; 2 sec. to ignition. | Not sensitive |
| t-Butyl Peroxy 2-Chlorolaurate | 93.84 | Vigorous decomposition between 106-½-117° C., with initial decomposition at 103° C. | 35 sec. with mild sooty flame between ¼-⅜ft; 19 sec. to ignition. | Not sensitive |
| 1,1,3,3-Tetramethyl Butyl Peroxy 2-Chlorolaurate | 92.43 | Very vigorous decomposition between 99-½-103° C., with initial decomposition at 97-¼° C. | 69 sec. with mild sooty Flame to 1 ft. Match served as a wick in final portions of burning; 2 sec. to ignition. | Not sensitive |
| 2,5-Dimethyl-2,5-Di(2-Chlorolauroyl Peroxy) Hexane | 95.33 | Mild explosion at 109-½° C., with initial decomposition at 98° C. and mild decomposition at 105° C. | 76 sec. with same results as above. | Not sensitive |

[1] 30 drops of product in alternate sample holes in an aluminum block; heated at 4° C. per minute.
[2] 1 g. of product in a #5 Coors procelain crucible; ignited with a match.
[3] 2 drops of product on a paper towel and hit with a hammer.

The following table illustrates the desirable half lives obtainable with compositions of this invention:

Table 3

Ten Hour Half-Life Temperatures of Various 2-Chloroalkyl Peresters
0.2 M in Benzene

| Perester | Ten Hour Half-Life Temp. ° C |
|---|---|
| 1. 1,1,3,3-Tetramethyl butyl peroxy 2-chlorolaurate | 65 |
| 2. 2,5-Dimethyl-2,5-di(2-chloro butyryl peroxy) hexyne-3 | 71.5 |
| 3. 2,5-Dimethyl-2,5-di(2-chloro lauroyl peroxy) hexane | 74.5 |
| 4. t-Butyl peroxy 2-chlorolaurate | 77.0 |
| 5. t-Butyl Peroxy 2-chlorooctanoate | 77.5 |
| 6. t-Butyl peroxy 2-chlorobutyrate | 81.7 |
| 7. t-Butyl peroxy 2-bromolaurate | 85 |

The present compositions are efficient polymerization initiators for ethylenically unsaturated monomers as mentioned above. Typical of their performance is their efficiency for the polymerization or curing of unsaturated polyester resins. Typical polymerization results are shown in Table 4:

The above performance of the peroxyesters of this invention is even more surprising when considering that substantial improvements are shown at reduced molar concentrations. If a comparison at equal molar concentrations is made, even greater improvements in efficiency will be obtained.

In Table 5 below results of a normal pot-life test are reported. Pot-life is the amount of time that elapses before gel occurs with a particular polyester resin containing peroxide. An extended pot-life is advantageous in applications utilizing polyesters. Derivatives of 1,1,3,3-tetramethyl butyl hydroperoxide as exemplified by 1,1,3,3-tetramethyl butyl peroxy 2-chlorolaurate have particularly desirable longer pot-lives.

Table 5

Pot Life with Various 2-Chloroalkyl Peresters in GR941 Polyester Resin at Room Temperature
$4.62 \times 10^{-3}$ moles/100 g. resin with monoperesters; ½ molar levels with diperesters. All levels adjusted to 100% purity.

| Peroxide Used | % wt | Pot-Life, Days |
|---|---|---|
| Set 1 | | |
| 1. 2,5-Dimethyl-2,5- | 0.89 | ~1.1 |

Table 4

Hot Block Gel Tests with Various 2-Chloroalkyl Peresters; 1%wt. Perester (Adjusted to 100% Purity) in 50 g. GR941 Resin[1]; 250° F. at Time Zero

| Perester Used | Moles/100 g. Resin | Gel Time | Exotherm Time | Peak Temperature ° C. |
|---|---|---|---|---|
| Set 1 | | | | |
| 1. 1,1,3,3-Tetramethyl butyl peroxy 2-Chlorolaurate | $2.75 \times 10^{-3}$ | 1'28" | 2'07" | 187.7 |
| 2. 2,5-Dimethyl-2,5-di-(2-chlorolauroyl peroxy) hexane | $1.64 \times 10^{-3}$ | 1'35" | 2'12" | 181.4 |
| 3. t-Butyl peroxy 2-chlorooctanoate | $3.99 \times 10^{-3}$ | 1'41" | 2'20" | 189.4 |
| 4. t-Butyl peroxy 2-chlorobutyrate | $5.14 \times 10^{-3}$ | 1'39" | 2'17" | 184.5 |
| 5. t-Butyl peroxy 2-chloropropionate | $5.54 \times 10^{-3}$ | 1'43" | 2'23" | 190.0 |
| Set 2 | | | | |
| 1. 2,5-Dimethyl-2,5-di-(2-chlorolauroyl peroxy) hexyne-3 | $2.61 \times 10^{-3}$ | 1'32" | 2'05" | 181.7 |
| 2. t-Butyl peroxy 2-chlorolaurate | $3.26 \times 10^{-3}$ | 1'39" | 2'13" | 183.6 |
| 3. t-Butyl peroxy 2-chloropropionate | $5.54 \times 10^{-3}$ | 1'43" | 2'18" | 188.9 |

[1] Unsaturated polyester containing styrene monomer.

Table 5-continued

Pot Life with Various 2-Chloroalkyl Peresters
in GR941 Polyester Resin at Room Temperature
4.62 × 10⁻³ moles/100 g. resin with monoperesters; ½ molar
levels with diperesters. All levels adjusted to 100% purity.

| Peroxide Used | % wt | Pot-Life, Days |
|---|---|---|
| di(2-chlorobutyryl peroxy)hexyne-3 | | |
| 2. 2,5-Dimethyl-2,5- di(2-chlorolauroyl peroxy)hexane | 1.42 | ~3 |
| 3. t-Butyl peroxy 2-chlorooctanoate | 1.16 | ~1.5 |
| 4. t-Butyl peroxy 2-chlorobutyrate | 0.90 | ~2.5 |
| 5. t-Butyl peroxy 2-chloropropionate | 0.83 | 2.5 |
| Set 2[1] | | |
| 1. 1,1,3,3-tetramethyl butyl peroxy 2-chlorolaurate | 1.68 | 10 |
| 2. t-Butyl peroxy 2-chlorolaurate | 1.42 | 5 |
| 3. t-Butyl peroxy 2-chloropropionate | 0.83 | ~4.5 |

[1] New sample of resin.

The following table is a comparison of ten-hour half lives of the new molecules of this invention with closely related alternatives. As can be seen from the ten-hour half life figures, the choice of an alpha halo substituent serves to control thermal stability of the molecule.

t-butyl peroxyisobutyrate has been included as an example of a commerically used perester than can be replaced by the present molecules because of its similar half life but otherwise undesirable properties.

Table 6

Comparison of Half-Lifes of Various Monoperesters
(0.2 M in Benzene)

| Initiator | 10 Hour Half-Life Temp., °C | Half-Life at 85° C | Time in Hours at 90° C* |
|---|---|---|---|
| t-butylperoxy 2-ethyl butyrate | 73.8 | | 1.15 |
| t-butyl peroxy 2-methyl pentanoate | 74.5 | | 1.5 |
| t-butyl peroxy 2-chloro butyrate | 81.7 | 6.83 | 3.6 |
| t-butyl peroxy- pentanoate | 97 | | 26.0 |
| t-butyl peroxy 2-ethyl hexanoate | 73.8 | | 1.3 |
| t-butyl peroxy 2-chloro octanoate | 77.5 | 4.05 | 2.3 |
| t-butyl peroxy nonanoate | 97 | | 22.5 |
| t-butyl peroxy 2-chloro laurate | 77 | 3.77 | 2.25 |
| t-butyl peroxy- decanoate | 98 | | 26.4 |
| t-butyl peroxy- isobutyrate | 78 | 3.6 | 2.0 |

*Most of the half lifes were taken from a semi-log plot of half life time v. reciprocal temperature.

Table 7 below provides half life data demonstrating that substituents in diperesters cause changes in thermal stability similar to that caused by the same substituents in the monoperester structure.

Table 7

Comparison of Half-Lifes of Various Disperesters
0.2 M in Benzene

| Initiator Structure | Alkyl Group | 10 Hour Half-Life Temp., °C |
|---|---|---|
| A[1] | 2-ethyl butyryl | 68 |
| B[2] | same | 65 |
| A | 2-methyl pentanoyl | 67 |
| B | same | 67 |
| A | 2-ethyl hexanoyl | 68 |
| B | same | 67 |
| A | pentanoyl | 90 |
| B | same | 95 |
| A | decanoyl | 93 |
| B | same | 95 |

[1] A = 2,5-dimethyl-2,5-di(alkyl peroxy)hexane
[2] B = 2,5-dimethyl-2,5-di(alkyl peroxy)hexyne-3

What is claimed is:

1. An organic peroxide of the formula:

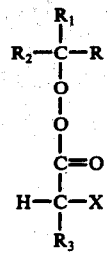

wherein each of R₁ and R₂ are alkyl of up to about 7 carbon atoms, X is selected from bromine and chlorine, R₃ is alkyl of up to about 18 carbon atoms provided that R₃ is not methyl when R is alkyl, and R is selected from alkyl of up to about 7 carbon atoms and

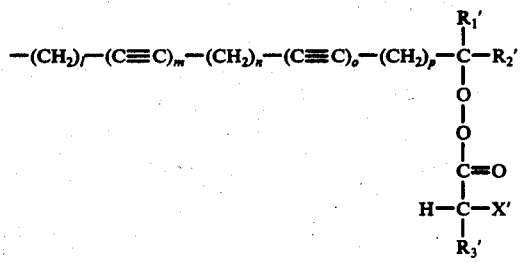

in which $l$, $m$, $n$, $o$, and $p$ are integers from 0–5 provided the sum of $l$, $m$, $n$, $o$, and $p$ is at least 1, and R₁', R₂' and R₃' are each the same as R₁, R₂ and R₃, respectively.

2. An organic peroxide in accordance with claim 1, wherein R is an alkyl group of up to about 7 carbon atoms.

3. An organic peroxide in accordance with claim 1, wherein R is the group

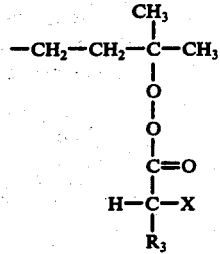

4. An organic peroxide in accordance with claim 1, wherein R is the group

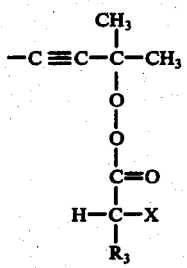

5. An organic peroxide in accordance with claim 1, wherein each of R, R₁ and R₂ is methyl.

6. An organic peroxide in accordance with claim 1, wherein each of R and $R_2$ is methyl and $R_1$ is 2,2-dimethyl propyl.

7. An organic peroxide in accordance with claim 1, wherein $R_3$ is an alkyl group of two to about 10 carbon atoms.

8. An organic peroxide in accordance with claim 1, wherein X is chlorine.

9. An organic peroxide in accordance with claim 1, wherein said peroxide is t-butyl peroxy 2-chlorobutyrate.

10. An organic peroxide in accordance with claim 1, wherein said peroxide is t-butyl peroxy 2-chlorooctanoate.

11. An organic peroxide in accordance with claim 1, wherein said peroxide is t-butyl peroxy 2-chlorolaurate.

12. An organic peroxide in accordance with claim 1, wherein said peroxide is 1,1,3,3-tetramethyl butyl peroxy 2-chlorolaurate.

13. An organic peroxide in accordance with claim 1, wherein said peroxide is 2,5-dimethyl-2,5-di(2-chlorolauroyl peroxy)hexane-.

14. An organic peroxide in accoradance with claim 1, wherein said peroxide is 2,5-dimethyl-2,5-di(2-chlorobutyryl peroxy)hexane-3.

15. An organic peroxide in accordance with claim 1, wherein said peroxide is t-butyl peroxy 2-bromolaurate.

16. An organic peroxide of the formula:

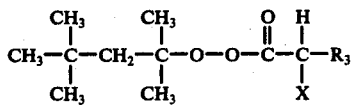

wherein X is selected from bromine and chlorine and $R_3$ is alkyl of up to about 18 carbon atoms.

* * * * *